United States Patent [19]
Koehler et al.

[11] Patent Number: 5,962,738
[45] Date of Patent: Oct. 5, 1999

[54] POLYMERIC-AMINE FUEL AND LUBRICANT ADDITIVE

[75] Inventors: Donald E. Koehler, Mentor; William J. Claffey, Novelty, both of Ohio

[73] Assignee: Petrokleen, Ltd., Cleveland, Ohio

[21] Appl. No.: 09/097,913

[22] Filed: Jun. 16, 1998

Related U.S. Application Data

[63] Continuation-in-part of application No. 08/710,684, Sep. 23, 1996, which is a continuation-in-part of application No. 08/356,700, Dec. 15, 1994, Pat. No. 5,559,270.

[51] Int. Cl.$^6$ .................................................. C07C 209/06
[52] U.S. Cl. .......................... 564/355; 564/359; 564/546; 44/418; 44/432
[58] Field of Search ............................ 548/546; 564/355, 564/359; 44/418, 432; 508/293, 559

[56] References Cited

U.S. PATENT DOCUMENTS

| | | | |
|---|---|---|---|
| H1305 | 5/1994 | Townsend et al. | 44/449 |
| 3,275,544 | 9/1966 | Hendrik . | |
| 3,753,670 | 8/1973 | Strang et al. | 44/432 |
| 3,756,793 | 9/1973 | Robinson | 44/432 |
| 3,785,790 | 1/1974 | Strang | 44/432 |
| 3,822,209 | 7/1974 | Knapp et al. . | |
| 3,864,098 | 2/1975 | Honnen | 44/334 |
| 3,869,514 | 3/1975 | Miller et al. | 260/584 R |
| 3,876,704 | 4/1975 | Nakaguchi | 564/503 |
| 3,951,614 | 4/1976 | Honnen et al. | 44/331 |
| 4,191,537 | 3/1980 | Lewis et al. | 44/71 |
| 4,236,020 | 11/1980 | Lewis et al. | 560/159 |
| 4,357,148 | 11/1982 | Graiff | 44/432 |
| 4,832,702 | 5/1989 | Kummer | 44/62 |
| 4,859,210 | 8/1989 | Fraz, et al. | 44/432 |
| 4,906,252 | 3/1990 | Gutierrez et al. | 44/63 |
| 5,006,130 | 4/1991 | Aiello et al. | 44/432 |
| 5,399,178 | 3/1995 | Cherpeck | 44/415 |
| 5,482,522 | 1/1996 | Cherpeck | 44/391 |
| 5,518,511 | 5/1996 | Russell et al. | 44/347 |
| 5,559,270 | 9/1996 | Koehler et al. | 564/484 |

FOREIGN PATENT DOCUMENTS

| | | |
|---|---|---|
| 1083610 | 8/1966 | United Kingdom . |
| 1419957 | 6/1973 | United Kingdom . |

*Primary Examiner*—Brian M. Burn
*Attorney, Agent, or Firm*—Fay, Sharpe, Beall, Fagan, Minnich & McKee

[57] ABSTRACT

The present invention relates to an improved method of synthesizing polyamines, the improvement comprising producing polyamines having an increased nitrogen content. It concerns the improved fuel additives thereby produced, and the resultant improved fuel composition which comprises an admixture of said fuel additive and a gasoline.

17 Claims, No Drawings

POLYMERIC-AMINE FUEL AND LUBRICANT ADDITIVE

This is a continuation-in-part of Ser. No. 08/710,684, filed Sep. 23, 1996, which is a continuation-in-part of Ser. No. 08/356,700 filed Dec. 15, 1993, now U.S. Pat. No. 5,559,270.

BACKGROUND OF THE INVENTION

The present invention relates to an improved method of synthesizing polyamines, the improvement comprising producing polyamines having an increased nitrogen content. It concerns the improved fuel additives thereby produced, and the resultant improved fuel composition which comprises an admixture of said fuel additive and a gasoline.

It is known that oil soluble polyamines containing at least one olefinic polymer chain or oil soluble polyether can be employed to improve the detergent properties of fuel and lubricant compositions. The use of such compositions, their utility in providing a fuel with significantly reduced octane requirement increase (ORI) characteristics; removal and/or beneficial modification of deposits in the combustion chamber, intake valves and the like; as well as potential improvement in fuel efficiency are taught by a number of prior patents including U.S. Pat. Nos. 3,275,554; 4,438,757; 3,565,804; 3,574,576; 3,898,056; 3,960,515; 4,022,589; and 4,039,300, the disclosures and claims of all of which are specifically incorporated herein by reference. Such polyamines have been used both alone and in combination with other additives, particularly polymeric additives.

Polyolefinic or polyether amine fuel detergents are composed primarily of two components; a hydrophile (amine) and a long chain hydrocarbyl or oxyalkylene hydrophobes (polymer). The hydrophile portion, typically amines, contain from one to greater than five nitrogen atoms. The hydrocarbyl or oxyalkylene hydrophobe is typically a long chain (500–5,000 molecular weight) polymer offering thermal stability and fuel solubility to the detergent.

The detergent molecule is synthesized through a variety of unique processes. For fuel additive applications the desired reaction for maximum cost performance is 100% utilization of reaction component, reacting one polymer molecule with one amine molecule to create a monomeric product. However, many processes are designed for or are limited to 65% monomer when amines containing multiple reactive moieties are utilized. The remaining polymer either does not react or over reacts to dimer or higher homologs (i.e. molecules containing two or more polymer molecules attached to one amine molecule).

In every process, the polymer is first reacted, modified, conditioned or combined with specific reaction components to promote the reaction with an amine. Polymers and amines will not react without the intermediate step.

Various conversion processes for creating polyamines are described in the prior art. For example, U.S. Pat. Nos. 3,275,554; 3,864,098; 3,565,804; 3,753,670; 3,822,209; 3,869,514; 4,438,757 and 5,346,965 all relate to the following conversion of polyisobutene (PIB) to PIB-amine.

PRIOR ART EXAMPLE 1

Polyisobutene (PIB+Chlorine→Chlorinated Polyisobutene (PIB-Cl) PIB-Cl+amine→PIB-amine+Bis-PIB-amine (i.e., PIB-amine-PIB,aka. dimer)

The patent literature generally indicated that less than 65% PIB-amine monomer is generated when using this type of process with amines containing multiple reactive nitrogen. The following table represents PIB-amine yield from U.S. patent literature:

| U.S. Pat. No. | Assigned To | Amine | PIB-amine %* | Multiple reactive nitrogen |
|---|---|---|---|---|
| 4,055,402 | BP | AEEA | 72.2% | no |
| 5,346,965 | FERRO/KIEL | AEEA | 72.0% | no |
| 3,869,514 | TEXACO | AEEA | 67.8% | no |
| 3,753,670 | SHELL | DMAPA | 61.2% | no |
| 4,055,402 | BP | AEEA | 60.0% | no |
| 3,822,209 | ETHYL | DMA | 65.0% | no |
| 3,565,804 | CHEVRON | EDA | 64.4% | yes |
| 5,346,965 | FERRO/KIEL | EDA | 63.8% | yes |
| 3,565,804 | CHEVRON | TEPA | 57.0% | yes |
| 3,438,757 | CHEVRON | TEPA | 41.0% | yes |
| 3,565,804 | CHEVRON | TETA | 25.0% | yes |
| 3,438,757 | CHEVRON | EDA | 31.0% | yes |
| 3,864,098 | CHEVRON | diamino-pyradine | 25.0% | yes |
| 3,275,554 | SHELL | TEPA | 7.0% | yes |

*Monomeric PIB-amine assumes at least 5% unreacted PIB or PIB-Cl

Another prior art process for preparing polyamines is a process wherein a polyalkylene, such as PIB, is first reacted with an anhydride, such as maleic anhydride, wherein the resulting product is then reacted with an amine. The example set forth below is representative of such a reaction:

PRIOR ART EXAMPLE 2

PIB+maleic anhydride→Polyisobutenylsuccinic anhydrine (PIBSA) PIBSA+ amine→Monosuccinimide and Bis-succinimide graphically presented below:
(graphics from: Union Carbide brochure, "Ethyleneamines")

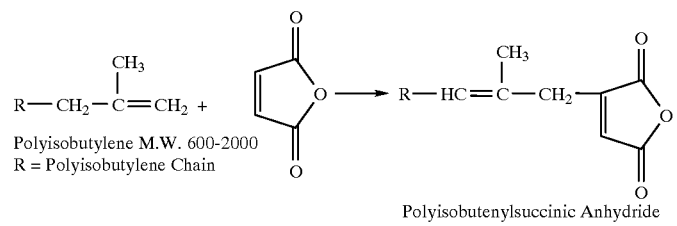

Polyisobutylene M.W. 600-2000
R = Polyisobutylene Chain

Polyisobutenylsuccinic Anhydride

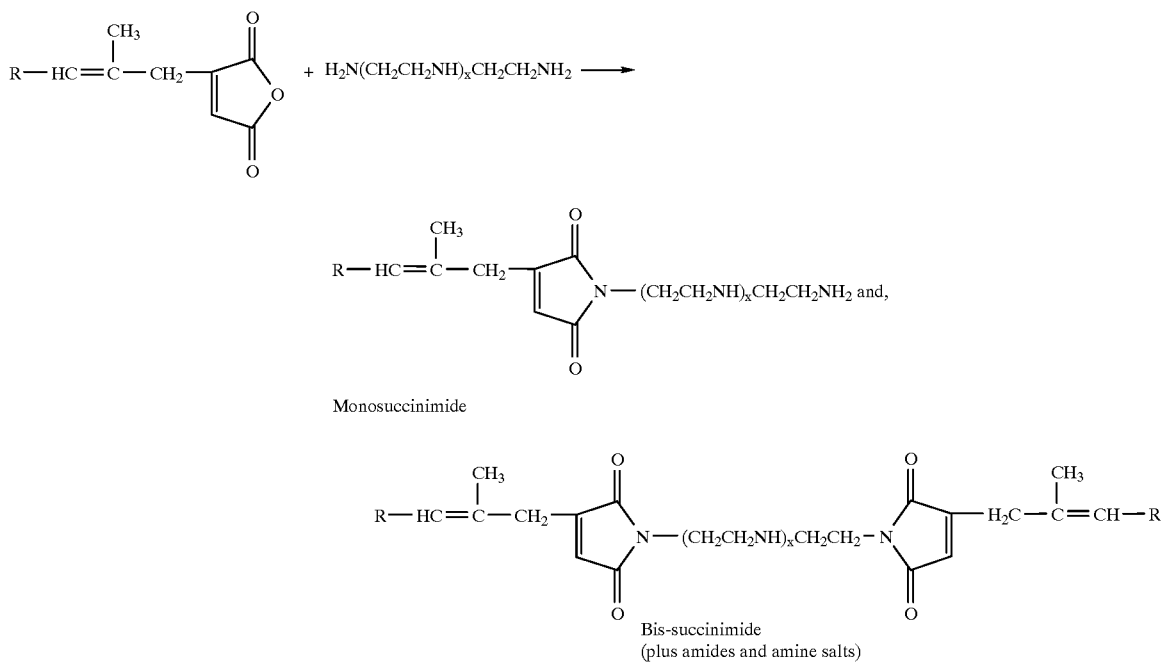

Monosuccinimide

Bis-succinimide
(plus amides and amine salts)

The patent literature (U.S. Pat. No. 4,906,252 and U.S. Pat. No. 5,518,511) teaches that cross-linking and reaction of multiple reactive amine moieties result in an expected monosuccinimide concentration of less than 50%.

Another prior art process used for preparation of polyamines involves reacting a polymeric compound, for example a polyalkyl compound, with a phenol to form a alkyl-phenol. The alkylphenol is then reacted with formaldehyde and an amine to form an alkyl phenol amine (also known as a Mannich Base) and a bis-alkyl phenol amine. The following example is representative of such a reaction:

PRIOR ART EXAMPLE 3

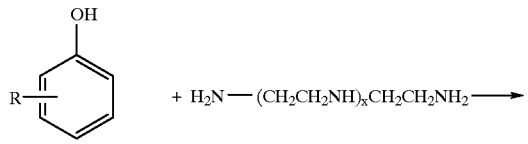

Alkylphenol
R = hydrocarbyl with
40-100 carbon atoms

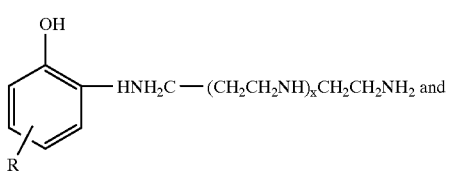

-continued

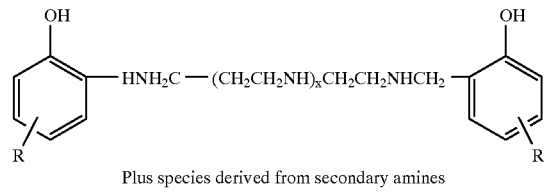

Plus species derived from secondary amines

The patent literature (U.S. Pat. No. 5,039,310) indicated that less than 50% Monoalkylphenolamine is generated when using this type of process.

In addition, each of the examples below are typical prior art processes for generating polyamines wherein undesirable bis-product is generated along with the desirable mono-polymeric amine:

PRIOR ART EXAMPLE 4

Polyoxyalkyl (POA)+phenol→POA-phenol POA-phenol+formaldehyde+amine→POA phenol amine
(aka. Mannich base)+Bis-POA phenol amine The patent literature (U.S. Pat. No. 5,399,178 and U.S. Pat. No. 5,482,522) indicates that commercial reaction products typically produce a mixture of products because of competing or sequential reactions which result in secondary and derivative products, such as cross-linked products. As a result, it is difficult to accurately determine the concentration of monomeric structure. Isolation of any particular product is not economical due to inherent limitations in controlling specific structure types using the process according to the prior art literature set forth above.

PRIOR ART EXAMPLE 5

POA+phosgene→POA-CL POA-Cl+amine→POA-amine+Bis-POA-amine (i.e. POA-amine-POA)

The patent literature (U.S. Pat. No. 4,191,537 and U.S. Pat. No. 4,236,020) indicated that less than 50% mono-POA-amine is generated when using this type of process.

PRIOR ART EXAMPLE 6

PIB+CO+$H_2$→PIB aldehyde (PIBa)+PIB alcohol (PIBa1) PIBa+PIBa1+amine→PIBa-amine+PIBa-amine+Bis-PIBa1-amine-PIBa1 and/or PIBa-amine-PIBa The patent literature (U.S. Pat. No. 4,832,702) calculates chemical conversion in terms of reacted PIB. This approach does not account for the concentration of specific molecular structure, i.e. monomer/dimer. Rather, it infers that reacted PIB is preferred, independent of molecular structure.

From the examples provided, it is believed that the use of mixed amine technology according to the present invention will significantly increase the conversion of PIB while simultaneously controlling the molecular structure to monomer.

In each example of the process of reacting a polymer with an amine containing reactive amines (i.e. containing multiple reaction sites), bis material is formed. Bis material deteriorates economics, handling properties and can significantly deteriorate overall performance.

The bis component is made up of unreacted and over reacted polymer components. The unreacted polymer has not been functionalized by the amination reaction and therefore will not function as a detergent. In the over reacted component (dimer), the preferred characteristics have been eliminated. In addition, the dimer reduces possible reaction sites limiting the opportunity to incorporate additional amine groups. Furthermore, the approximate doubling of molecular weight increases viscosity.

Increasing the concentration and molecular weight of polymer independent of its source increases the concern for additive related deposits when the detergent is used in an engine. This requires additional solvent and carrier fluid to balance overall additive performance. The result is a larger package, increased treat cost and potential additive deposits in the engine.

One of the primary elements of defining the value of detergents is the concentration of nitrogen. The monomer components has the highest concentration, the dimer contains approximately half that of the monomer and the unreacted contains zero. The manufacturing penalty associated with bis components is inversely proportional to their concentration.

Until now, those additives that are manufactured to maximize monomer concentration have generally been produced by reacting a polyolefinic halide with a substantial stoichiometric excess of amine to reduce, though not totally eliminate, the formation of dimers and trimers. The use of such stoichiometric excess of amine, however, results in a substantial negative impact to the manufacturing costs because of the significant quantity of excess amine that must be continuously purified and recycled, and because of the reduction in effective reactor volume.

SUMMARY OF THE INVENTION

The present invention provides a method of synthesizing polyolefinic amines, having a reduced concentration of dimers and/or trimers. It comprises the steps of:

(a) providing a reactive polymer which has been conditioned to react with an amine;

(b) reacting the reactive polymer of step (a) with from about 0.01 to about 0.99 molar equivalent of a polyamine having only one reactive amine for a period of from about 0.5 to about 15.0 hours at a temperature of from about 75° F. to about 410° F. at a pressure of from about 0 to about 6 atmospheres;

(c) adding to said reaction mass at least one additional polyamine having at least two primary amine moieties, in an amount equal to from about 0.01 to about 10.0 times the molar quantity of reactive polymer employed to form a second reaction mass and reacting said second reaction mass for a period of from about 1 to about 15 hours at a temperature of from about 75° F. to about 410° F. at a pressure of from about 0 to about 6 atmospheres;

(d) distilling off any unreacted polyamine at a distillation temperature of below about 400° F.; and, (e) treating said second reaction mass to recover the polymeric-amine products.

The present invention also encompasses the fuel additive product produced by the foregoing process, and the novel motor fuel composition containing an amount of this additive of 0.5–5.0 ppm, expressed as basic nitrogen. This will inhibit octane requirement increase (ORI) and clean up the induction system.

In accordance with the present invention, a separate step is incorporated between the polymer conditioning and primary amination. The sequential use of selected amines preaminates a portion of the polymer to the desired "mono" structure and blocks the over reaction of the preaminated polymer. This step has two benefits: first, a portion of the reactive polymer is converted to the desired structure and secondly, in the primary amination, the ratio of reactive polymer to amine is shifted to maximize reaction to the mono structure without the extreme excess amine.

Thus an advantage of the process according to this invention is that it will significantly increase control of the reaction thus generating more of the desired molecular structure in the resulting product. The idea is applicable to processes reacting amines containing more than one reactive nitrogen. Several processes from the patent literature which may be modified according to the process of this invention to produce the desired mono-polymeric amine products, have been described above.

DETAILED DESCRIPTION OF THE INVENTION

In the process of the present invention, the formation of increased nitrogen concentration in a polymeric-amine fuel and lubricant additive is accomplished by incorporating a separate pre-amination step between a polymer conditioning step and a primary amination step in conventional polymeric-amine conversion reactions. This pre-amination step reduces or eliminates formation of the over reacted (dimer) portion of the bis-component and replaces it with the more desirable mono-component which thereby increases the available nitrogen concentration for a detergent composition used in fuels and lubricants.

The process of the present invention is applicable to any process wherein amines containing multiple reaction sites are currently used.

Various polymeric agents are useable as starting materials in the conversion process of the present invention. Examples of such polymeric agents useable as starting materials include, but are not limited to, polyolefins, polyoxyalkylenes, and polyethers.

Examples of polyolefins which may be used as starting materials in accordance with the present invention include, but are not limited to, one or more olefinic polymers derived from alkanes or alkenes with straight or branched chains, which may or may not have aromatic or cycloaliphatic substituents, for instance, groups derived from polymers or copolymers of olefins which may or may not have a double bond. Examples of non-substituted alkenyl and alkyl groups are polyethylene groups, polypropylene groups, polybutylene groups, polyisobutylene groups, polyethylene-polypropylene groups, polyethylene-poly-alpha-methylstyrene groups and the corresponding groups without double bonds. Particularly preferred are polypropylene and especially polyisobutylene groups, or oil soluble polyethers such as copolymers of ethylene oxide and propylene oxide.

Suitable polyoxyalkylenes useable as starting materials in the process according to the present invention include, but are not limited to, for example those described in U.S. Pat. No. 4,191,537, U.S. Pat. No. 4,236,020 and U.S. Pat. No. 5,482,522 each of whose disclosure is incorporated herein by reference.

The poly(oxyalkylene) polymers useable in the present invention comprise of one or more poly(oxyalkylene) polymers composed of oxyalkylene units containing from 2 to about 5 carbon atoms. The oxyalkylene units contain from 3 to 4 carbon atoms. Each poly(oxyalkylene) polymer contains at least about 5 oxyalkylene units, preferably 8 to about 100 oxyalkylene units, more preferably about 10–100 units and most preferably 10 to about 25 such units. In general, the oxyalkylene units may be branched or unbranched. Preferably the poly(oxyalkylene) polymer chain contains at least some $C_3$–$C_5$ oxyalkylene units. More preferably, branched $C_3$–$C_5$ oxyalkylene units are present in at least sufficient number to render the poly(oxyalkylene) amine soluble in the fuel composition of the present invention. This solubility condition is satisfied if the polyamine is soluble in hydrocarbons boiling in the gasoline range, at least to the extent of about 30–2,000 ppm by weight. A poly(oxyalkylene) polymer chain composed of branched three and/or four carbon oxyalkylene units in at least sufficient amount to effect the solubility in the fuel composition is most preferred. The structures of the $C_3$–$C_5$ oxyalkylene units are any of the isomeric structures well know to the organic chemist, e.g., n-propylene, isopropylene, n-butylene, sec butylene, tert-butylene, disec-butylene, isobutylene, etc. The preferred poly(oxyalkylene)compounds are composed, at least in part, of the branched oxyalkylene isomers, particularly oxy(isopropylene) and oxy(sec-butylene) units which are obtained from 1,2-propylene oxide and from 1,2-butylene oxide, respectively.

Among the various polyethers useable as starting materials in the present invention are polyethers, polyetheroxides and polyetherglycols.

In accordance with the practice of the present invention, the polymeric starting materials are initially conditioned to be reactive with an amine. Conditioning takes place by reacting the polymeric starting material with materials such as halogens, anhydrides, phenols, phosgene, carbon monoxide/$H_2$ etc. to produce a polymeric compound containing a terminal portion which is reactive with an amine.

The polyamines used to form the polyamine compounds of this invention include primary, secondary, and tertiary low molecular weight aliphatic polyamines such as ethylene diamine, diethylenetriamine, triethylenetetramine, dimethylaminopropylamine, propylene diamine, butylene diamine, trimethyl trimethylene diamine, tetramethylene diamine, diaminopentane or pentamethylene diamine, hexamethylene diamine, heptamethylene diamine, diaminooctane, decamethylene diamine, and higher homologues up to about 10 carbon atoms. In the preparation of these compounds, the same amines can be used or substituted amines can be used such as N-methyl ethylene diamine, N-propyl ehtylene diamine, N,N-dimethyl 1,3-propane diamine, N-2-hydroxypropyl ethylene diamine, penta-(1-methylpropylene)hexamine, tetrabutylene-pentamine, hexa(1,1-dimethylethylene)heptane, di-(1-methylamylene) triamine, tetra-(1,3-dimethylpropylene) pentamine, penta(1,5-dimethylamylene)hexamine, di(1-methyl-4 -ethylbutylene)triamine, penta-(1,2-dimethyl-1-isopropyl-ethylene)hexamine, tetraoctylenepentamine and the like.

Compounds possessing triamine as well as tetramine and pentamine groups are applicable for use because these can be prepared from technical mixtures of polyethylene polyamines, which could offer economic advantages.

The polyamine can be a cyclic polyamine, for instance, the cyclic polyamines formed when aliphatic polyamines with nitrogen atoms separated by ethylene groups were heated in the presence of hydrogen chloride.

The unexpected realization of the increased production of the desired mono-polymeric amine is accomplished when the conditioned polymer described above is initially modified by a pre-amination step prior to a second amination step. The pre-amination step is comprised of reacting the polymer which has been conditioned to react with an amine with a polyamine having only one reactive amine. Preferably, the polyamine having only one reactive amine is used at rates of from about 0.01 to about 0.99 molar equivalents. The reaction time can be from about 0.5 to about 15.0 hours at a temperature of from about 75° F. to about 410° F. Pressure in the reaction system can range from about 0 to about 6 atmospheres.

Suitable polyamines, having only a single primary amine, useable in the pre-amination step set forth above include, but are not limited to, polyamines in which all other amine moieties are hindered, such as DMAPA (dimethyaminopropylamine).

In a second amination reaction step, the pre-aminated polymer is subjected to an additional polyamine having at least two primary amine moieties such as EDA (ethylenediamine) or tetramethylene pentamine. Preferably, the polyamine having at least two primary amine moieties is present in an amount of from about 0.01 to about 10.0 times the molar quantity of reactive polymer employed in the preamination step. This forms a second reaction mass which is reacted for a period of from about 1 to about 15 hours at a temperature of from about 75° F. to about 410° F. and a pressure of from about 0 to about 6 atmospheres.

As specific illustrations of the preparation of products by the process in the present invention, the following examples are presented by way of illustration and not by way of limitation.

Preparation of Polymeric Halides

In a flask, 1000 grams of the desired polyolefin having an average molecular weight of 950 was contacted with about 97 grams of chlorine gas. The temperature was maintained between 95 and 105° C. for about 4 hours. A 30 minute nitrogen purge was used to remove suspended chlorine and HCl from the polyolefinic halide (the chlorine analysis was determined to be 4.7%).

Example 1

Into a 4 liter high pressure autoclave, 1,147 grams of polyolefinic halide (produced as described) was transferred via a pressure bomb. Immediately following this, 692 grams of ethylene diamine was added to the autoclave via a second pressure bomb. The autoclave was sealed and pressurized to about 60 PSIG and the temperature increased to 170° C. with constant stirring. This temperature was maintained for about 5 hours. A portion of the material was transferred to a flask where the free amine was distilled. Aqueous sodium hydroxide was added to free the amine reacted with the amine·HCl salts. Following this, water and free amine were distilled. A portion of the mixture was transferred to a high pressure filter for separation of the solids.

Several attempts were made to filter the solids:
  Attempt A: #1 Watman filter paper, no filter aid, 75 PSIG, unable to filter
  Attempt B: #1 Watman filter paper, with filter aid #1, 75 PSIG, unable to filter
  Attempt C: #1 Watman filter paper, with filter aid #2, 40 PSIG, able to filter 30 ml after½ hour.

Analysis of filtered material showed: 2.3 % nitrogen, 1300 ppm of ionic chloride.

Significance: The nitrogen analysis demonstrates that the process is effective at reacting polyolefinic halide with ethylene diamine; however, the solids produced during the reaction could not be easily filtered. The 1300 ppm of ionic chloride in the polyolefinic amine is unacceptable. This experiment demonstrates the reasons most polyolefinic amine manufacturing relies upon a series of water/butanol wash steps to remove the finely dispersed solids.

Example 2

In a flask, 99 grams of polyolefinic halide (produced as previously described) were reacted with 25 grams of dimethylaminopropylamine at a temperature of 125° C. for about 100 minutes with constant stirring; 15 grams of ethylene diamine was added to the polyolefinic halide dimethylaminopropylamine mixture. The flask temperature was increased to about 145° C. over a period of 200 minutes with stirring and reflux. The total reaction time was 300 minutes. Following the reaction, the reflux equipment was replaced with distillation equipment and the free amine removed as the temperature was increased to about 160° C. The flask was cooled to 70° C. and aqueous sodium hydroxide was added at a stoichiometric excess of 1.1 to 1.2 relative to the initial polyolefinic halide. The mixture was stirred as the temperature was increased to 160° C. as the water and free amine (amine freed from the amine·HCl salts) were distilled. The material in the flask was clear and bright, with a dark straw color, with a layer of solids at the bottom. A sample was decanted from the flask and analyzed for nitrogen and chlorine and found to contain 2.3% nitrogen and 90 ppm ionic chloride. A portion of the sample was filtered through #1 Watman filter paper without filter aid. A portion was centrifuged. The filtered and centrifuge samples contained the same concentration of ionic chloride and nitrogen.

Significance: The results demonstrate that the process described in this example effectively reacts polyolefinic halide with ethylene diamine and the solids can be easily filtered from the polyolefinic amine.

Additional analysis was conducted to verify that the sample described by Example 2 was free of dimers and trimers. Gel permeation chromatography (GPC) analysis was conducted. For reference, unreacted polyolefin and a commercial polyolefinic amine are presented. The number average molecular wt., Mn was selected as the characteristic most descriptive for these samples.

| Sample | Mn | % Difference |
| --- | --- | --- |
| A. Unreated polyolefin | 1,097 | N.A. |
| B. Example 2 sample | 1,071 | −2.4 |
| C. Commerical sample | 1,952 | +77.9 |

Significance: The results demonstrate that the sample from Example 2 did not increase Mn, verifying that crosslinking producing dimers and trimers did not occur.

The 2.4% difference between A and B is within experimental variability. The commercial sample C showed a 77.9% increase relative to the unreacted polyolefin.

Further analysis combining the GPC results with nitrogen analysis for the polyolefinic amines (B and C) demonstrates that sample B contains about 65% more reacted nitrogen than sample C. This difference is due to the reduced number of polyolefinic halide reactions sites resulting from the formation of dimers and trimers during the manufacturing of C.

Example 3

In a flask, 95 grams of polyolefinic halide (produced as previously described) was reacted with 24 grams of dimethylamino propylamine (2.5 molar ratio of PIB-chloride to DMAPA) at a temperature of 125° C. for 100 minutes with stirring and reflux; 45 grams of tetraethylenepentamine was added to the polyolefinic halide demethylaminopropylene mixture. The flask temperature was increased to about 145° C. over a period of 200 minutes with stirring and reflux. The total reaction time was 300 minutes. Following the reaction, the reflux equipment was replaced with distillation equipment and the free dimethylaminopropylamine was removed. The contents were transferred to a pressure funnel with #1 Watman filter paper and the amine·HCl crystals were separated from the polyolefinic amine. The amine·HCl crystals were transferred to a clean flask and aqueous NaOH was added at a stoichiometric excess to recover the amine. The water and dimethylaminopropylamine were distilled and the tetraethylenepentamine was filtered from the solids. Analysis of the polyolefinic amine after simple filtration through #1 Watman filter paper without filter aid and less than 5 PSIG pressure showed 3.1% nitrogen and about 100 ppm of ionic chloride.

The following examples are representative of additional processes according to the present invention wherein the mixed amine technology (preamination step) is employed.

Example 4
PIB+maleic anhydride→Polyisobutenylsuccinic anhydrine (PIBSA)
The final product should contain significantly higher amine concentration than Prior Art Example 2, set forth above, and no dimer.
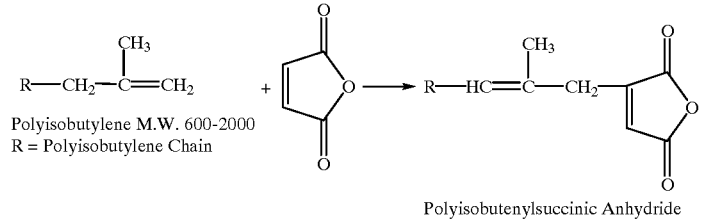
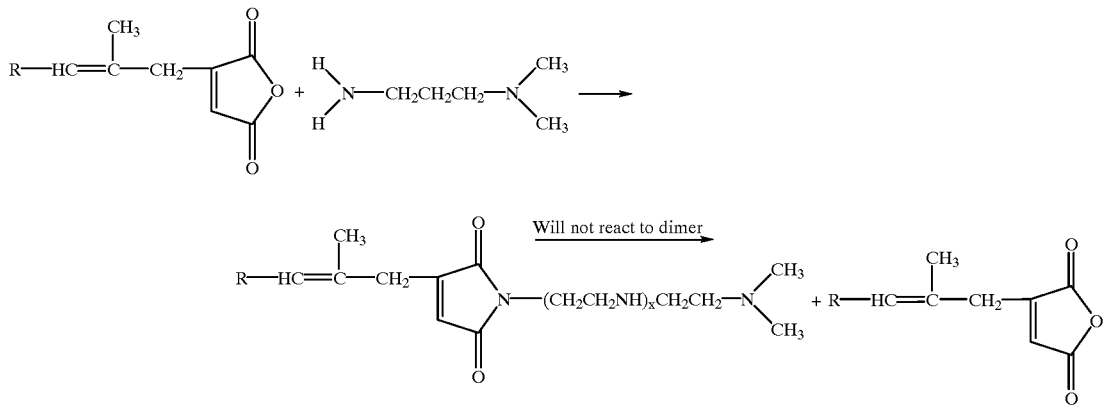
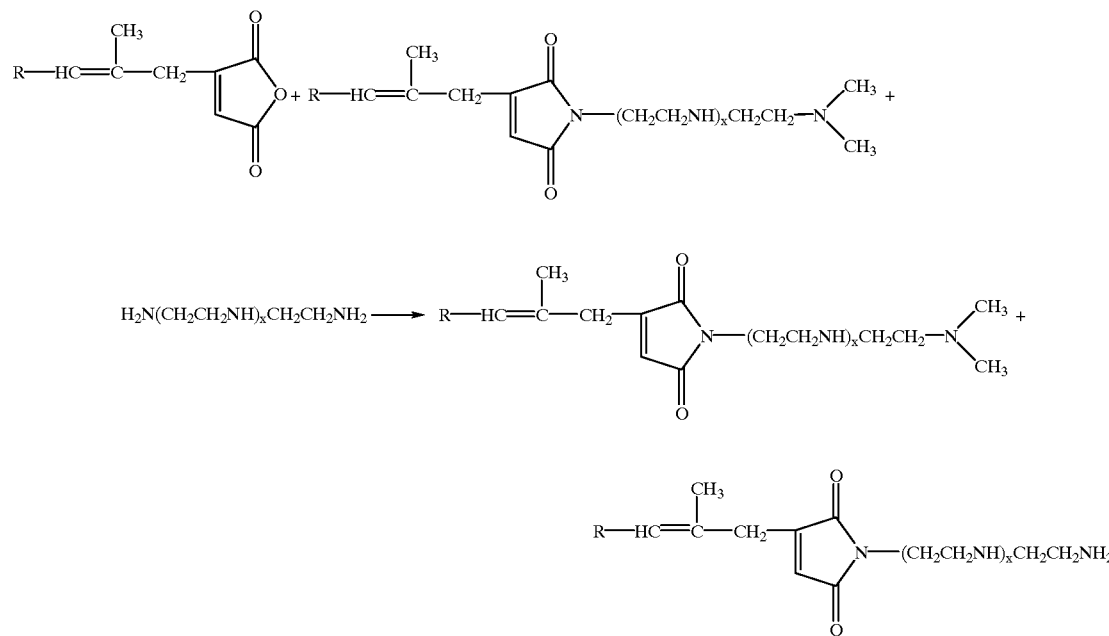

Example 5

PIB+phenol→alkyl phenol (AP) AP+
formaldehyde+dimethylaminopropylamine
(DMAPA)→alkyl phenol-DMAPA (aka. Mannich
base)+AP+formaldehyde (NO DIMER DUE TO
TERMINAL TERTIARY NITROGEN)

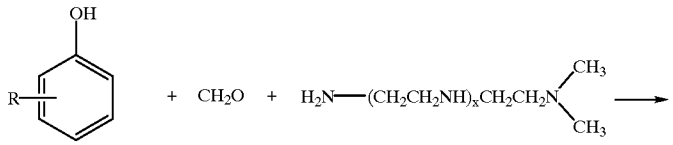

Alkylphenol
R = hydrocarbyl with
40-100 carbon atoms

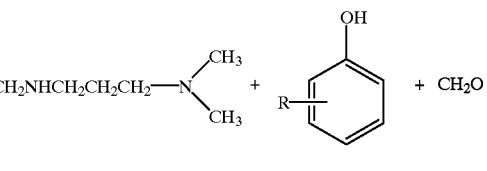

alkyl-phenol-DMAPA(Mannich base) + AP + formaldehyde + diethylenetriamine ⟶ alkyl phenol-DMAPA + alkyl phenol-DETA

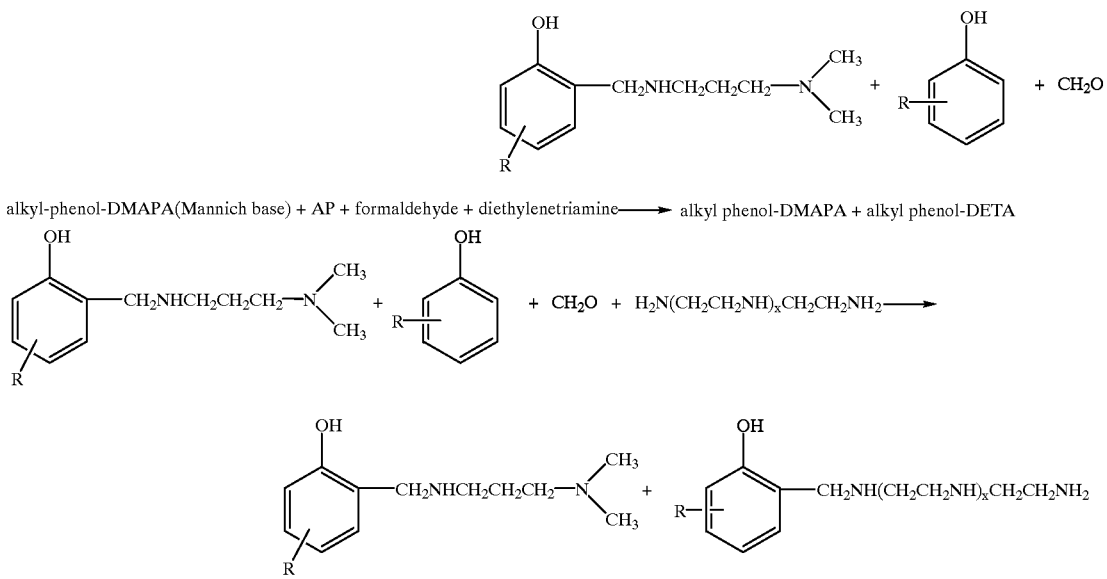

The final product should contain significantly higher amine concentration than Prior Art Example 3, set forth above, and no dimer.

It is commonly accepted in the art that liquid hydrocarbon distillate fuel compositions containing polyamines such as those produced according to the present invention effectively counteract, nullify and/or inhibit fouling of vital parts of internal combustion engines.

The invention demonstrates a method to eliminate formation of the over reacted (dimer) portion of the bis detergent component and replace it with desirable mono component, providing improved economics and performance. The invention is applicable to any process reacting highly reactive amines containing multiple reaction sites.

The process of the present invention will carry out the objects set forth hereinabove. It is, therefore, to be understood that any variations evident fall within the scope of the claimed invention and thus, the selection of specific reactants as well as processing conditions can be determined without departing from the spirit of the invention herein disclosed and described. In particular, deposit control fuel additives according to the present invention are not necessarily limited to those having the amines exemplified herein or the mole ratios employed. Moreover, as noted hereinabove, other reaction temperatures can be substituted for those disclosed herein. Thus, the scope of the invention shall include all modifications and variations that may fall within the scope of the attached claims.

Having thus described the invention, it is claimed:

1. A method of increasing the nitrogen concentration of a polymeric-amine fuel and lubricant additive comprising:
    (a) providing a reactive polymer which has been conditioned to react with an amine;
    (b) reacting the reactive polymer of step (a) with from about 0.01 to about 0.99 molar equivalent of a polyamine having only one reactive amine for a period of from about 0.5 to about 15.0 hours at a temperature of from about 75° F. to about 410° F. at a pressure of from about 0 to about 6 atmospheres to form a first reaction mass;
    (c) adding to said first reaction mass at least one additional polyamine having at least two primary amine moieties, in an amount equal to from about 0.01 to about 10.0 times the molar quantity of reactive polymer employed in step (b) to form a second reaction mass and reacting said second reaction mass for a period of from about 1 to about 15 hours at a temperature of from about 75° F. to about 410° F. at a pressure of from about 0 to about 6 atmospheres;
    (d) distilling off any unreacted polyamine at a distillation temperature of below about 400° F.; and,
    (e) treating said second reaction mass to recover the polymeric-amine products.

2. The method of claim 1 wherein the reactive polymer in step (a) is at least one polymer selected from the group consisting of:
    (a) polymeric halides;
    (b) polymeric anhydrides;

(c) polymeric phenols; and, (d) a mixture of polymeric aldehydes and polymeric alcohols.

3. The method of claim 2 wherein the reactive polymer (a)–(d) is a polyolefinic or polyoxyalkyl reactive polymer.

4. The method of claim 3 wherein the polyolefin is polyisobutene.

5. The method of claim 2 wherein the polymeric halide is polyisobutene-chloride.

6. The method of claim 2 wherein the polymeric anhydride is polyolefinic or polyoxyalkyl succinic anhydride.

7. The method of claim 6 wherein the polyolefinic succinic anhydride is polyisobutene succinic anhydride.

8. The method according to claim 1 wherein said first reacting step is carried out for from about 0.5 to about 3 hours at a temperature of from about 175° F. to about 360° F. at a pressure of from about 1 to about 6 atmospheres and said second reacting step is carried out in the presence of a molar excess of amine in the range of from 3 to about 8 times the molar quantity of reactive polymer employed to form the first reaction mass and for from about 2 to about 5 hours at a temperature of from about 175° F. to about 360° F. at a pressure of from about 0 to about 6 atmospheres.

9. The method of claim 1 wherein any unreacted polyamine remaining in said second reaction mass after said distillation step is reacted with HCl to convert the unreacted polyamine to polyamine-HCl.

10. The method according to claim 1 wherein said first reacting step employs DMAPA and said second reacting step employs a mixture of DMAPA and EDA in a molar ratio of from about 1:10 to about 10:1.

11. A method of manufacturing a polymeric amine fuel or lubricant additive wherein said polymeric-amine fuel or lubricant additive is comprised of at least about 90% of a polymeric-amine having a maximum of one polymer chain per amine unit, the method comprising:

(a) providing a reactive polymer which has been conditioned to react with an amine;

(b) reacting the reactive polymer of step (a) with from about 0.01 to about 0.99 molar equivalent of a polyamine having only one reactive amine for a period of from about 0.5 to about 15.0 hours at a temperature of from about 75° F. to about 410° F. at a pressure of from about 0 to about 6 atmospheres to form a first reaction mass;

(c) adding to said first reaction mass at least one additional polyamine having at least two primary amine moieties, in an amount equal to from about 0.01 to about 10.0 times the molar quantity of reactive polymer employed in step (b) to form a second reaction mass and reacting said second reaction mass for a period of from about 1 to about 15 hours at a temperature of from about 75° F. to about 410° F. at a pressure of from about 0 to about 6 atmospheres;

(d) distilling off any unreacted polyamine at a distillation temperature of below about 400° F.; and, (e) treating said second reaction mass to recover the polymeric-amine products.

12. A process for controlling cross linking and over reaction components produced during the manufacture of polymeric-amine fuel and lubricant additives said process comprising:

(a) providing a reactive polymer which has been conditioned to react with an amine;

(b) reacting the reactive polymer of step (a) with from about 0.01 to about 0.99 molar equivalent of a polyamine having only one reactive amine for a period of from about 0.5 to about 15.0 hours at a temperature of from about 75° F. to about 410° F. at a pressure of from about 0 to about 6 atmospheres to form a first reaction mass;

(c) adding to said first reaction mass at least one additional polyamine having at least two primary amine moieties, in an amount equal to from about 0.01 to about 10.0 times the molar quantity of reactive polymer employed in step (b) to form a second reaction mass and reacting said second reaction mass for a period of from about 1 to about 15 hours at a temperature of from about 75° F. to about 410° F. at a pressure of from about 0 to about 6 atmospheres;

(d) distilling off any unreacted polyamine at a distillation temperature of below about 400° F.; and, (e) treating said second reaction mass to recover the polymeric-amine products.

13. A polymeric-amine fuel or lubricant additive produced by the method of claim 11, wherein said polymeric-amine fuel or lubricant additive is comprised of at least about 90% of a polymeric-amine having a maximum of one polymer chain per amine unit.

14. The polymer-amine fuel or lubricant additive according to claim 13 further comprising one or more additional fuel or lubricant additive components selected from the group consisting of (i) a polymer of a $C_2$ to $C_4$ mono-olefin, (ii) a copolymer of a $C_2$ to $C_4$ mono-olefin, (iii) the corresponding hydrogenated polymer or copolymer, (iv) an oil soluble poly(oxyalkylene) alcohol, glycol or polyol or a mono or di ether thereof, which has the formula $R_1$—O—$(R_2O)_n$—$R_3$ wherein $R_1$ and $R_3$ each independently is a hydrogen atom or an aliphatic, cycloaliphatic or mononuclear aromatic hydrocarbon group of up to 40 carbon atoms, $R_2$ represents an alkaline group and n is an integer of at least 7, (v) a naphthenic or paraffinic oil having a viscosity of 100 C. of from about 2 to about 15 centistokes wherein the fuel or lubricant additive components (i)–(iv) are present in an amount of up to 600 ppmw.

15. The polymeric-amine fuel or lubricant additive according to claim 13 further comprising additional components selected from the group consisting of demulsifiers, corrosion inhibitors, and fuel stabilizers.

16. The polymeric-amine fuel or lubricant additive according to claim 13 further comprising other detergent based systems selected from polyalkyl amines, polyether amines, polyalkylsuccinimide, polyalkylaminophenol, and/or low molecular weight amines said other detergent based systems being included in the composition to enhance cleanliness, performance, and/or economics of the composition.

17. A method for controlling and reducing carburetor, fuel injector, intake valve and combustion chamber deposits in internal combustion engines comprising adding a polymeric-amine fuel or lubricant additive of any one of claims 13–16 to a fuel or lubricant for said internal combustion engine.

* * * * *